(12) United States Patent
Taguchi et al.

(10) Patent No.: US 7,842,343 B2
(45) Date of Patent: Nov. 30, 2010

(54) METHOD OF PRODUCING ANALYTICAL TOOL

(75) Inventors: Takayuki Taguchi, Kyoto (JP); Shigeru Kitamura, Kyoto (JP); Yuichiro Noda, Kyoto (JP); Toshio Takama, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1132 days.

(21) Appl. No.: 10/529,321

(22) PCT Filed: Sep. 25, 2003

(86) PCT No.: PCT/JP03/12296

§ 371 (c)(1),
(2), (4) Date: Mar. 25, 2005

(87) PCT Pub. No.: WO2004/029632

PCT Pub. Date: Apr. 8, 2004

(65) Prior Publication Data

US 2006/0118403 A1 Jun. 8, 2006

(30) Foreign Application Priority Data

Sep. 26, 2002 (JP) ............................. 2002-281102

(51) Int. Cl.
*C23C 16/08* (2006.01)
(52) U.S. Cl. ............................ 427/255.39; 427/255.23; 427/255.28; 525/330.3
(58) Field of Classification Search ........................ None
See application file for complete search history.

(56) References Cited

U.S. PATENT DOCUMENTS

| | | |
|---|---|---|
| 5,951,950 A | 9/1999 | Fukuoka et al. |
| 6,419,995 B1* | 7/2002 | Kuckertz et al. ............ 427/536 |
| 2002/0092767 A1* | 7/2002 | Bjornson et al. ............ 204/451 |
| 2002/0125135 A1* | 9/2002 | Derand et al. ............... 204/454 |
| 2003/0159945 A1 | 8/2003 | Miyazaki et al. |

(Continued)

FOREIGN PATENT DOCUMENTS

EP 1 085 317 6/1999

(Continued)

OTHER PUBLICATIONS

Hruska et al, "Ageing of the oxyfluorinated polypropylene surface: evolution of the acid-base surface characteristics with time," (2000),Journal of Fluorine Chemistry 105 87-93.*

*Primary Examiner*—Michael Cleveland
*Assistant Examiner*—Joel G Horning
(74) *Attorney, Agent, or Firm*—Hamre, Schumann, Mueller & Larson, P.C.

(57) ABSTRACT

The invention relates to a method of producing an analytical tool having recesses (20) formed therein for moving a sample liquid, a base plate (2) made of polymeric material, and a cover laminated to the base plate (2) to cover the recesses (20). This producing method includes the step of applying a hydrophilic treatment to the inner surfaces of the recesses (20). The hydrophilic treatment includes a primary modifying operation for primarily modifying the properties of the inner surfaces of the recesses (20) by contacting a modifying gas with the inner surfaces of the recesses (20), and a secondary modifying operation for secondarily modifying the properties of the inner surfaces of the recesses (20).

15 Claims, 7 Drawing Sheets

U.S. PATENT DOCUMENTS

2004/0016642 A1   1/2004   Miyazaki et al.

FOREIGN PATENT DOCUMENTS

| | | |
|---|---|---|
| EP | 1 235 068 | 11/2000 |
| JP | 60088044 A  * | 5/1985 |
| JP | 10-38875 | 2/1998 |
| JP | 2001-159618 | 6/2001 |
| JP | 2001-294692 | 10/2001 |
| JP | 2001294692 A  * | 10/2001 |
| JP | 2002-168821 | 6/2002 |
| JP | 2002-227074 | 8/2002 |
| WO | WO 99/64849 | 12/1999 |
| WO | WO 01/36954 | 5/2001 |

* cited by examiner

METHOD OF PRODUCING ANALYTICAL TOOL

TECHNICAL FIELD

The present invention relates to a method of producing an analytical tool which is used for analyzing a sample liquid and which is structured to move the sample liquid before the analysis.

BACKGROUND ART

Figure 9:
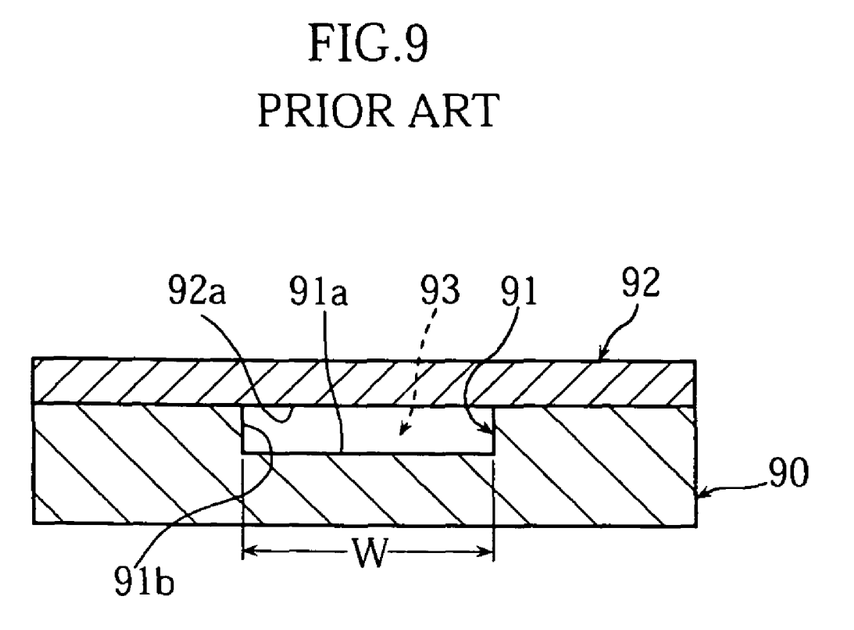
FIG. 9 is a sectional view of an analytical tool for describing a prior art method.

In one type of analytical tool, a sample liquid is caused to move by capillary action. Such an analytical tool includes a capillary for producing a capillary force. To properly exert the capillary force onto a sample liquid, the inner surface of the capillary is hydrophilically treated. For example, in the structure shown in FIG. 9, a capillary 93 is formed by covering a groove 91 formed in a substrate 90 with a cover 92. In this case, the bottom surface 91a of the groove 91 and one surface 92a of the cover 92 are hydrophilically treated. The hydrophilization treatment with respect to the inner surface of the capillary 93 may be performed by ultraviolet irradiation, the application of a surface-active agent or plasma discharge such as glow discharge or corona discharge, for example. (See JP-A 2001-159618 and JP-A 2002-168821, for example.)

Figure 10:
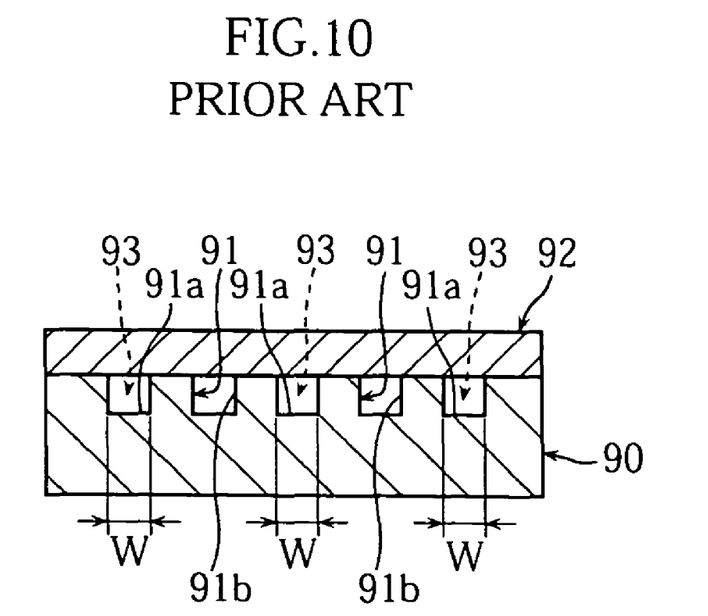
FIG. 10 is a sectional view of an analytical tool for describing a prior art method.

Recently, there is a tendency to reduce the sectional area of the capillary 93 to respond to the demand for the reduction of the amount of a sample liquid and the size reduction of an analytical tool. Particularly, in an analytical tool including a plurality of capillaries for analyzing a plurality of items, it is highly necessary to reduce the sectional area of each capillary. Since a typical analytical tool originally has a relatively small thickness, to effectively reduce the size of the analytical tool, the dimension of the tool as viewed in plan need be reduced. As shown in FIG. 10, to reduce the sectional area of each of capillaries 93 while reducing the size of the analytical tool as well, the width of each capillary 93 need be reduced. However, when the width of the capillary 93 is reduced to reduce the sectional area, the proportion of the hydrophilically-treated surfaces decreases in the case where hydrophilization treatment is performed only with respect to the bottom surface 91a of each groove 91 and to one surface 92a of the cover 92. Therefore, to properly move the sample liquid through the capillary 93, the hydrophilization treatment need be performed also with respect to the side surfaces 91b of the groove 91.

Figure 11A:
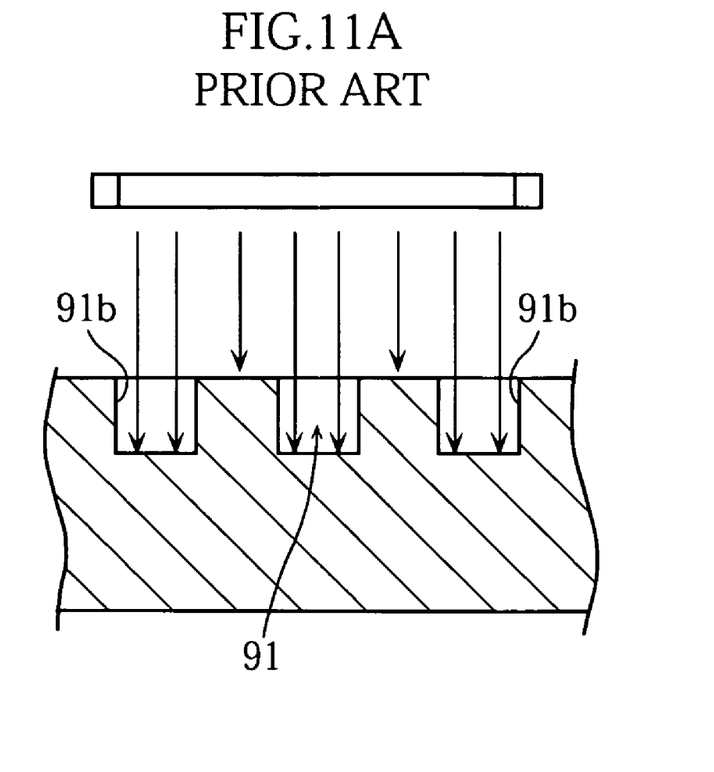
FIGS. 11A and 11B are sectional views for describing prior art hydrophilization treatment.

However, it is difficult to hydrophilically treat the side surfaces 91b of the groove 91 by the application of a surface-active agent or ultraviolet irradiation. Specifically, since light such as ultraviolet rays has linearity, it is difficult to cause ultraviolet rays to impinge on the side surface 91b of such a small flow path (groove) 91 as shown in FIG. 11A.

Figure 11B:
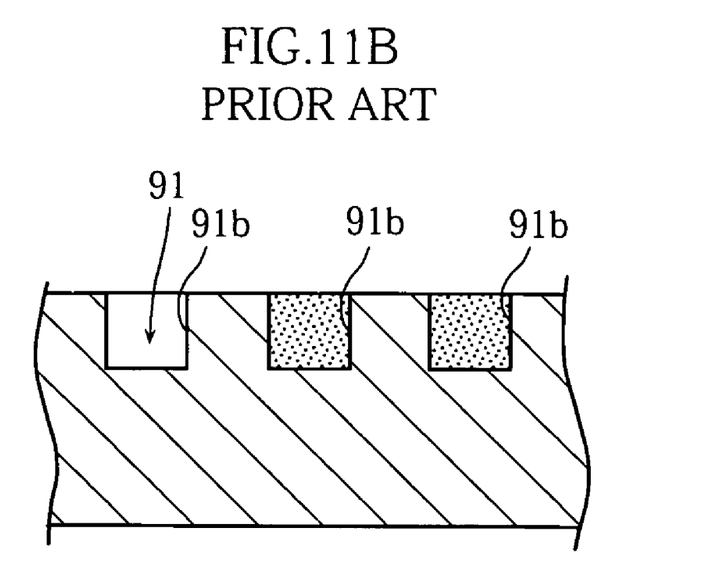

The hydrophilization treatment by the application of a surface-active agent is performed by supplying a liquid material containing a surface-active agent into the groove 91 and then drying the liquid material. Therefore, to apply the surface-active agent to the side surfaces 91b of the groove 91, it is necessary to completely fill the groove 91 with the liquid material and then dry the liquid material, as shown in FIG. 11B. In this way, since the groove 91 is filled with the surface-active agent to apply the surface-active agent to the side surface of the groove 91, the provision of a flow path having an intended sectional area is difficult.

The hydrophilization treatment by utilizing plasma discharge requires equipment for causing plasma discharge and hence requires high cost of equipment and manufacturing cost. Further, similarly to the hydrophilization treatment by ultraviolet irradiation, it is difficult to hydrophilically treat the side surfaces 91b of the groove 91 satisfactorily by plasma discharge.

DISCLOSURE OF THE INVENTION

An object of the present invention is to provide a method which is capable of properly performing hydrophilization even with respect to a small flow path without increasing the cost.

According to the present invention, there is provided a method of producing an analytical tool which comprises a substrate made of a polymer material and formed with a groove for moving a sample liquid, and a cover bonded to the substrate to cover the groove. The method comprises hydrophilically treating an inner surface of the groove. The hydrophilization treatment includes a primary modifying step for primarily modifying characteristics of the inner surface of the groove by bringing a modifying gas into contact with the inner surface of the groove, and a secondary modifying step for secondarily modifying the characteristics of the inner surface of the groove.

In the hydrophilization treatment, by the primary modifying step and the secondary modifying step, a carboxyl group, which is a hydrophilic group, is introduced into a polymer chain existing at a surface of the substrate, for example. Thus, the inner surface of the groove becomes hydrophilic. The degree of hydrophilization is such that the contact angle of pure water at the inner surface of the groove becomes 0~80 degrees, and preferably 0~60 degrees, for example.

The hydrophilization treatment may be performed before the cover is bonded to the substrate or after the cover is bonded to the substrate. In the latter case, when the cover is made of a polymer material, not only the inner surface of the groove but also the surface of the cover which faces the groove can be hydrophilically treated.

The primary modifying step may be performed for 1~60 minutes under such conditions that the partial pressure of the modifying gas is maintained at 10~2000 hPa and temperature is maintained at 0~100° C., and preferably, the partial pressure of the modifying gas is maintained at 100~1100 hPa and temperature is maintained at 0~40° C. Preferably, in the primary modifying step, use is made of a modifying gas containing fluorine gas and oxygen gas. Preferably, in this case, the mixing ratio of the fluorine gas and the oxygen gas is 1:1~1000 on a volume basis.

For example, the secondary modifying step comprises bringing water or water vapor into contact with the inner surface of the groove. The bringing of water or water vapor into contact with the inner surface of the groove may comprise spraying water or water vapor to an inner surface of the substrate or immersing the substrate in a water bath. The substrate may be brought into contact with air for secondarily modifying the inner surface of the groove by the moisture contained in the air. In this case, use may be made of air which has been positively caused to contain moisture.

The present invention is applicable to an analytical tool in which a sample liquid is caused to move by capillary action as a technique for making the inner surface of the fluid path hydrophilic. Particularly, the present invention is applicable to such an analytical tool as a microdevice which includes a small fluid path. For example, the present invention is applicable to a microdevice which includes a fluid path having a principal cross section (corresponding to the principal cross section of the groove of the substrate) having a rectangular shape which has a width W of 10~500 μm and a depth D of 5~500 μm and satisfies D/W≧0.5. The "principal cross section" herein indicates a vertical section extending perpendicularly to the travel direction of the sample liquid, and indicates the vertical section of a portion which is mainly utilized for traveling the sample liquid when the sectional configuration is not uniform.

In the present invention, the primary modifying step is performed by using modifying gas (gas), whereas the secondary modifying step is performed by using gas or liquid such as water vapor or water, for example. Since these substances do not have such linearity as that of ultraviolet rays, the substances such as modifying gas and water vapor can be reliably brought into contact with the inner surface of the groove of the substrate. Therefore, the entirety of the inner surface of the groove can be hydrophilically treated reliably. Such an advantage can be obtained also in producing a microdevice including a small flow path (a groove having a small sectional area). Moreover, since the apparatus for supplying modifying gas, water or water vapor can have a simple structure and can be manufactured at a low cost, the method is advantageous in terms of the manufacturing cost.

BEST MODE FOR CARRYING OUT THE INVENTION

The present invention relates to a method of producing an analytical tool which is mounted, in use, to an analytical apparatus. In the analytical apparatus, a sample liquid supplied to the analytical tool is analyzed by an optical method or an electrochemical method, for example.

FIGS. 1-4 show an example of analytical tool to be produced by a method according to the present invention. The analytical tool 1 shown in the figures is a so-called microdevice and designed to perform analysis of a sample by an optical method. The microdevice 1, which serves to provide a reaction field, includes a substrate 2 formed with a groove 20, and a cover 3 bonded to the substrate 2 via an adhesive sheet 4 to cover the groove 20.

Figure 1:
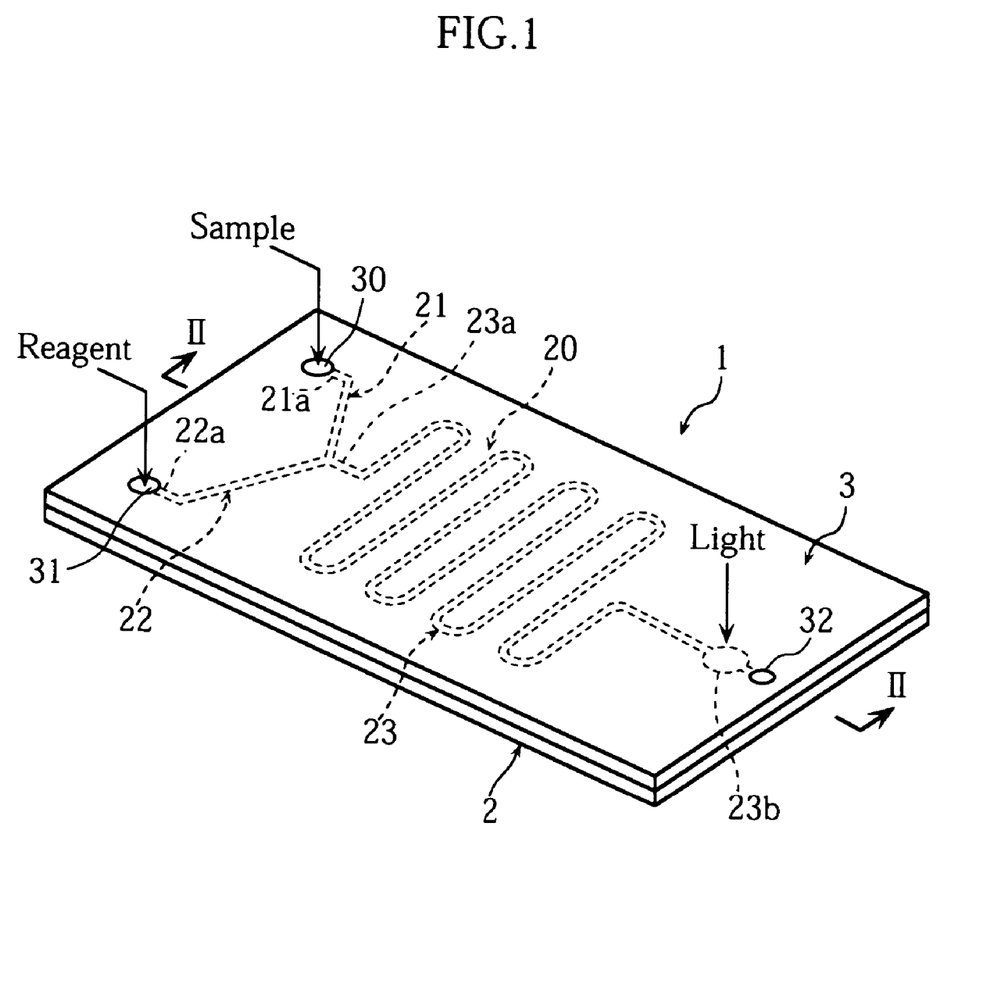
FIG. 1 an entire perspective view showing an example of microdevice as an object to be produced by the method of the present invention.
Figure 4:
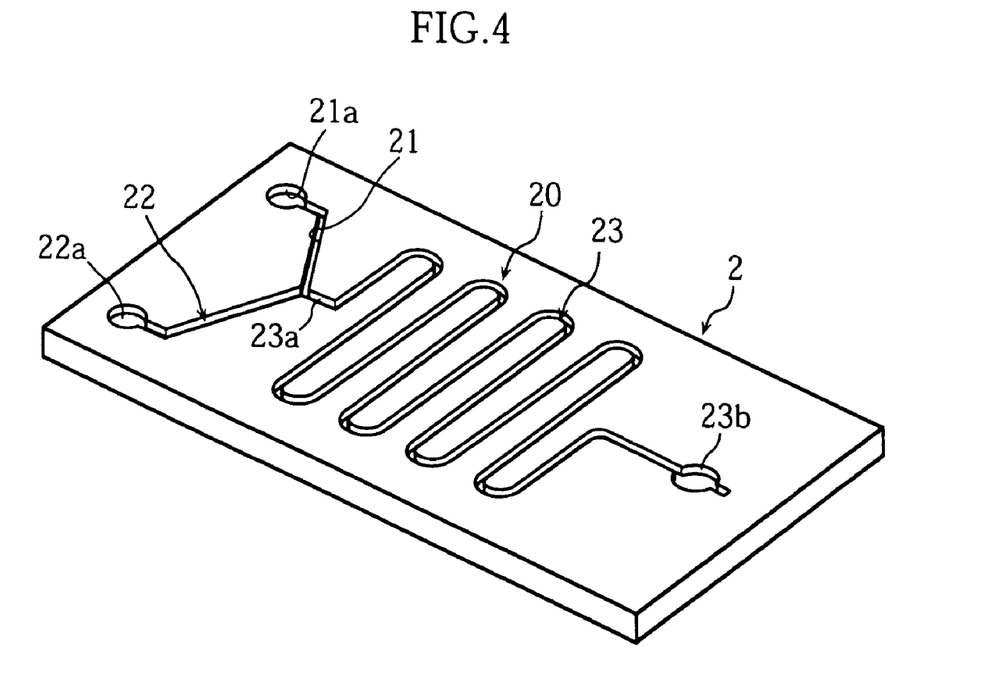
FIG. 4 is an entire perspective view showing the substrate of the microdevice.

As better shown in FIGS. 1 and 4, the groove 20 includes a sample introduction path 21, a reagent introduction path 22 and a reaction path 23. The reaction path 23 has an end 23a connected to the sample introduction path 21 and the reagent introduction path 22. The entirety of the reaction path 23 has a serpentine shape to have a long length. The reaction path 23 has another end 23b which provides a measurement portion to be irradiated with light from a measurement light source.

Figure 2:
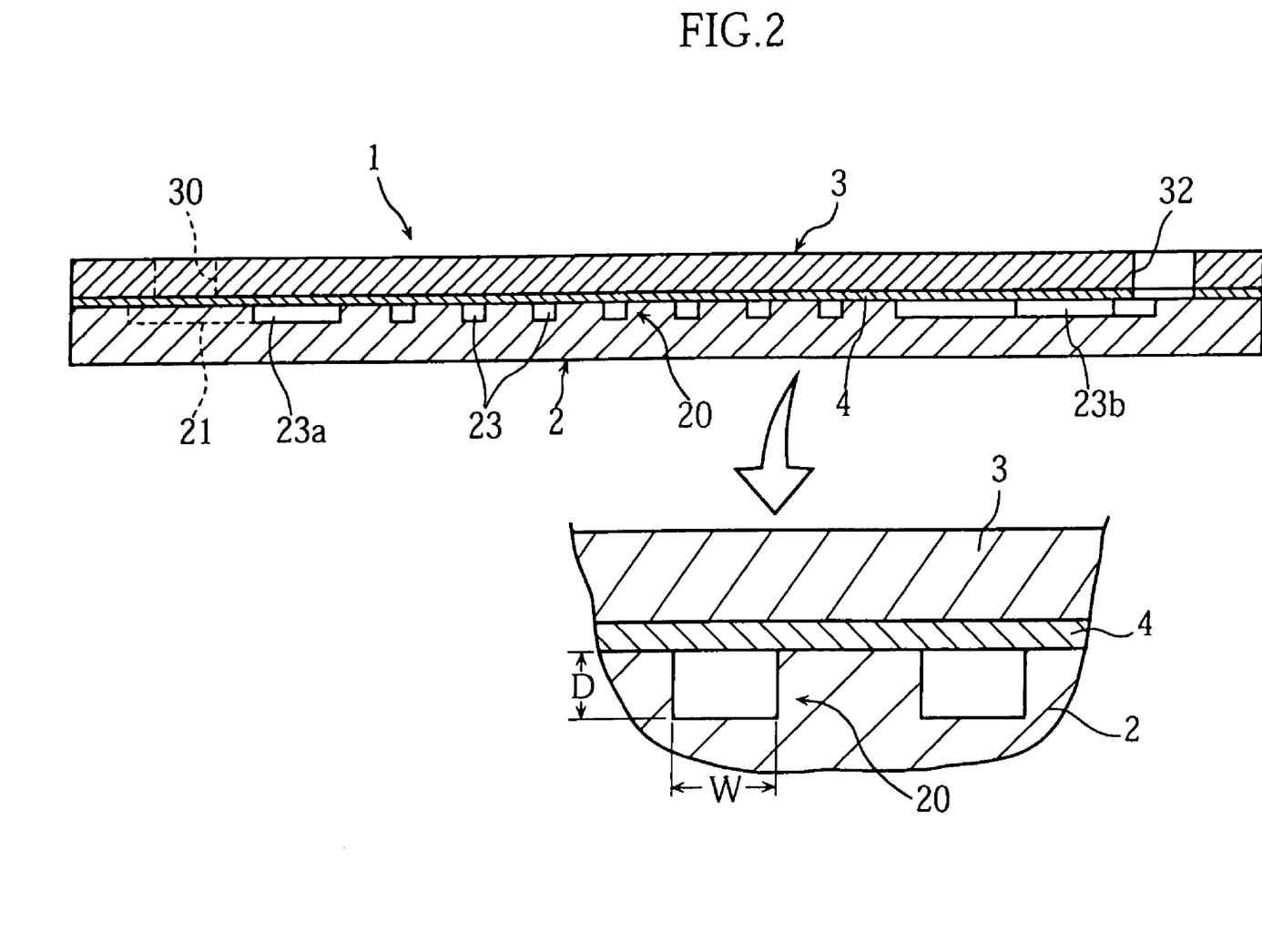
FIG. 2 is a sectional view taken along lines II-II in FIG. 1, part of which is shown as enlarged.

As shown in FIG. 2, the groove 20 has a principal rectangular cross section which has a width W of 10~500 μm and a depth D of 5~500 μm and which satisfies D/W≧0.5. The inner surface of the groove 20 is hydrophilically treated. The contact angle of pure water at the inner surface of the groove 20 is 0~80 degrees, for example.

Figure 3:
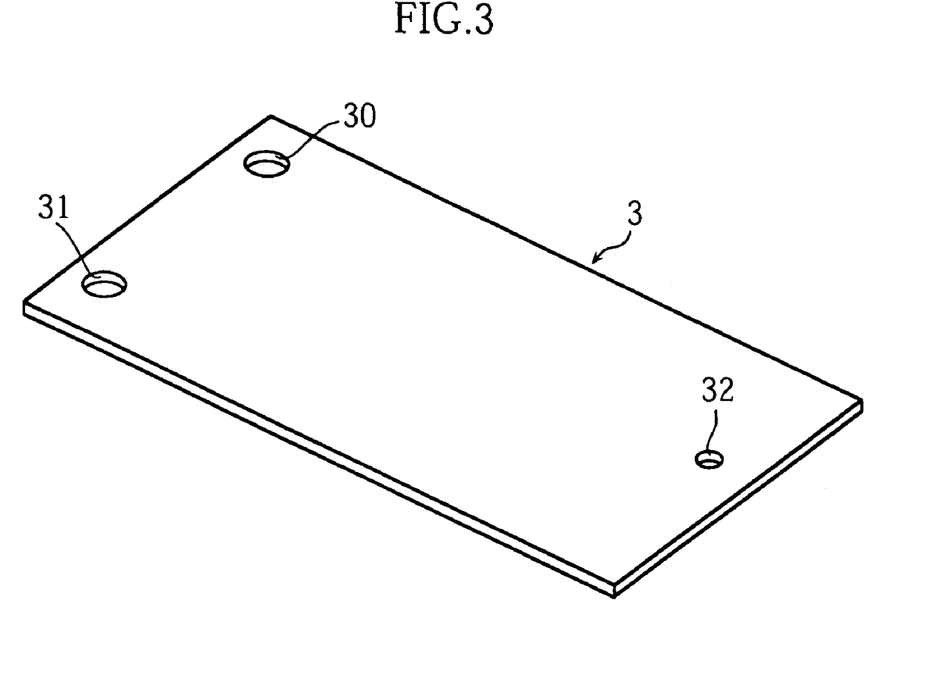
FIG. 3 is an entire perspective view showing the cover of the microdevice.

As shown in FIGS. 1 through 3, the cover 3 includes a sample introduction port 30, a reagent introduction port 31 and an air vent 32. The sample introduction port 30 is provided at a location corresponding to an end 21a of the sample introduction path 21, the reagent introduction port 31 provided at a location corresponding to an end 22a of the reagent introduction path 22, and the air vent 32 provided at a location corresponding to the end 23b of the reaction path 23.

For analyzing a sample, the sample and a reagent are introduced to the microdevice 1 through the sample introduction port 30 and the reagent introduction port 31, respectively. The sample and the reagent move, by capillary action, through the sample introduction path 21 and the reagent introduction path 22, respectively, to merge at the reaction path 23. As a result, reaction between the sample and the reagent starts. The sample and the reagent, while undergoing the reaction, travel through the reaction path 23 toward the air vent 23 by capillary action and finally reach the measurement portion 23b. At the measurement portion 23b, the reaction product of the sample and the reagent is analyzed by the analytical apparatus, as noted above.

A method of producing the microdevice 1 will be described below. Hereinafter, a method for producing a microdevice individually one by one will be exemplarily described.

The method of producing a microdevice 1 includes a cover forming step, a substrate forming step, a hydrophilization step and a bonding step.

In the cover forming step, a transparent resin film, for example, is subjected to punching and then cut into an intended size (See FIG. 3). By the punching, through-holes are formed, which are later to become the sample introduction port 30, the reagent introduction port 31 and the air vent 32. In the step for forming the cover 3, punching of the resin film may be performed after cutting of the resin film. One surface of the cover 3 may be hydrophilically treated by ultraviolet irradiation or the application of a surface-active agent. Examples of material of the resin film (material of the cover 3) include polymer materials such as polydimethylsiloxane (PDMS), polymethyl methacrylate (PMMA), polystyrene (PS), polycarbonate (PC) and polyethylene terephthalate (PET). The resin film (cover 3) may be made of a combination of at least two polymer materials. For example, the resin film (cover 3) may be made of a material provided by blending at least two of the polymer materials exemplified above. Alternatively, the resin film (cover 3) may be formed by bonding films or sheets which are made of different polymer materials together.

In the substrate forming step, a substrate is formed by injection molding using a thermoplastic resin, for example. In the injection molding, the groove 20 can be formed in the substrate 2 by appropriately designing the configuration of the mold. Alternatively, the groove 20 may be made by laser beam machining or etching, for example. Examples of material of the substrate include polymer materials such as polymethyl methacrylate (PMMA), polystyrene (PS), polycarbonate (PC) and polyethylene terephthalate (PET).

The hydrophilization step includes a primary modifying step for primarily modifying the characteristics of the inner surface of the groove 20 by bringing a modifying gas into contact with the inner surface of the groove 20, and a secondary modifying step for secondarily modifying the characteristics of the inner surface of the groove 20.

Figure 5:
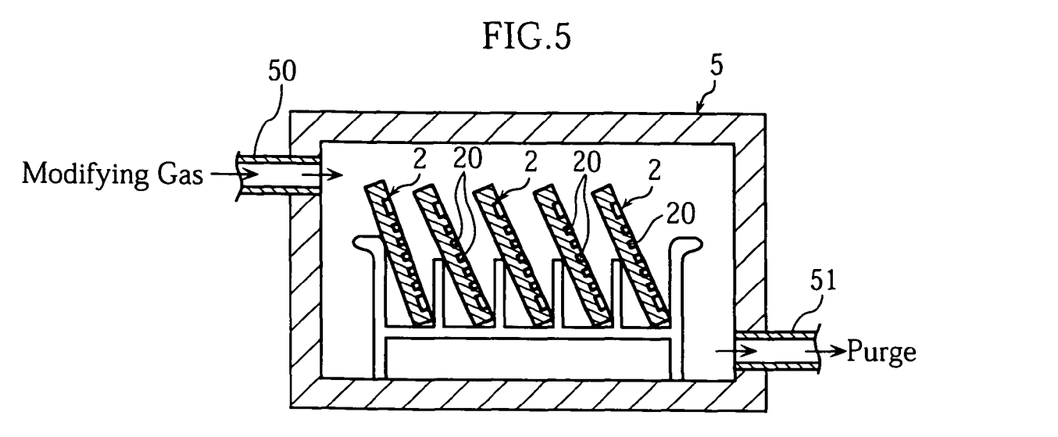
FIG. 5 is a sectional view showing a primary modifying step of the hydrophilization step in the production method of the present invention.

As shown in FIG. 5, for example, the primary modifying step is performed with a plurality of substrates 2 housed in a chamber 5. To the chamber 5 are connected a modifying gas supply pipe 50 for supplying the modifying gas to the chamber 5, and a purge pipe 51 for discharging gas from the chamber 5.

As the modifying gas, use may be made of gas containing fluorine gas and oxygen gas, for example. In this case, the mixing ratio of fluorine gas and oxygen gas is 1:1~1000, and preferably, 1:10~20 on a volume basis. During the primary modifying step, the interior of the chamber 5 is so maintained that the partial pressure of the modifying gas is 10~2000 hPa and the temperature is 0~100° C., and preferably, the partial pressure of the modifying gas is 100~1100 hPa and the temperature is 0~40° C. Under such conditions, the substrate 2 is kept in contact with the modifying gas for 1 to 60 minutes, for example. As a result, in a polymer chain forming the substrate 2, a fluorine atom is introduced to a side chain or an end group as bonded to a keto ketene group.

The secondary modifying step is performed by bringing water or water vapor into contact with the inner surface of the groove 20. As a result, the fluorine atom previously introduced is replaced with a hydroxyl group, whereby a carboxyl group is introduced into the polymer chain. Thus, the inner surface of the groove 20 becomes hydrophilic.

Figure 6:
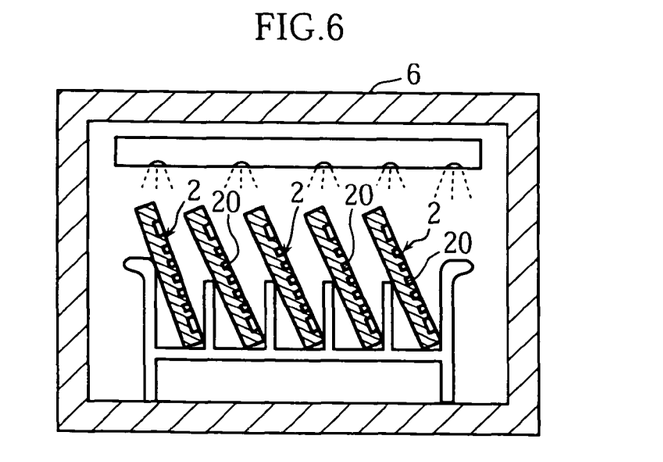
FIG. 6 is a sectional view showing a secondary modifying step of the hydrophilization step in the production method of the present invention.
Figure 7:
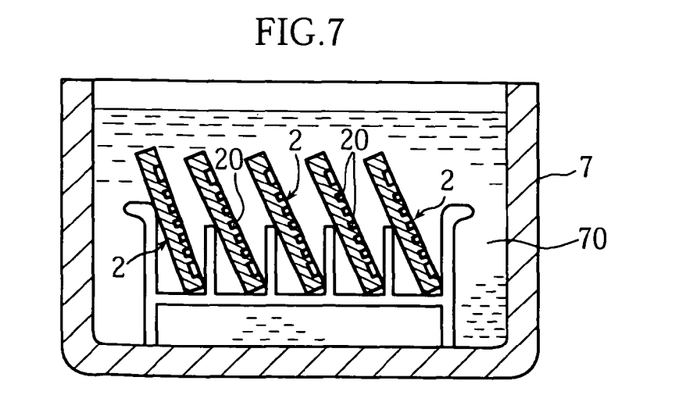
FIG. 7 is a sectional view showing another example of secondary modifying step of the hydrophilization step in the production method of the present invention.

For example, the contact of the inner surface of the groove 20 with water or water vapor may be performed by supplying water or water vapor to the chamber 6 accommodating the substrates 2, as shown in FIG. 6. The substrates 2 may be brought into contact with water or water vapor in an open system. The inner surface of the groove 20 may be brought into contact with water by immersing the substrates 2 in water 70 stored in a container 7, as shown in FIG. 7. The secondary modifying step may be performed by replacing the mixed gas contained in the chamber 6 with air to bring moisture contained in the air into contact with the inner surface of the groove 20. In this case, use may be made of air which has been positively caused to contain moisture or indoor air.

Figure 8:
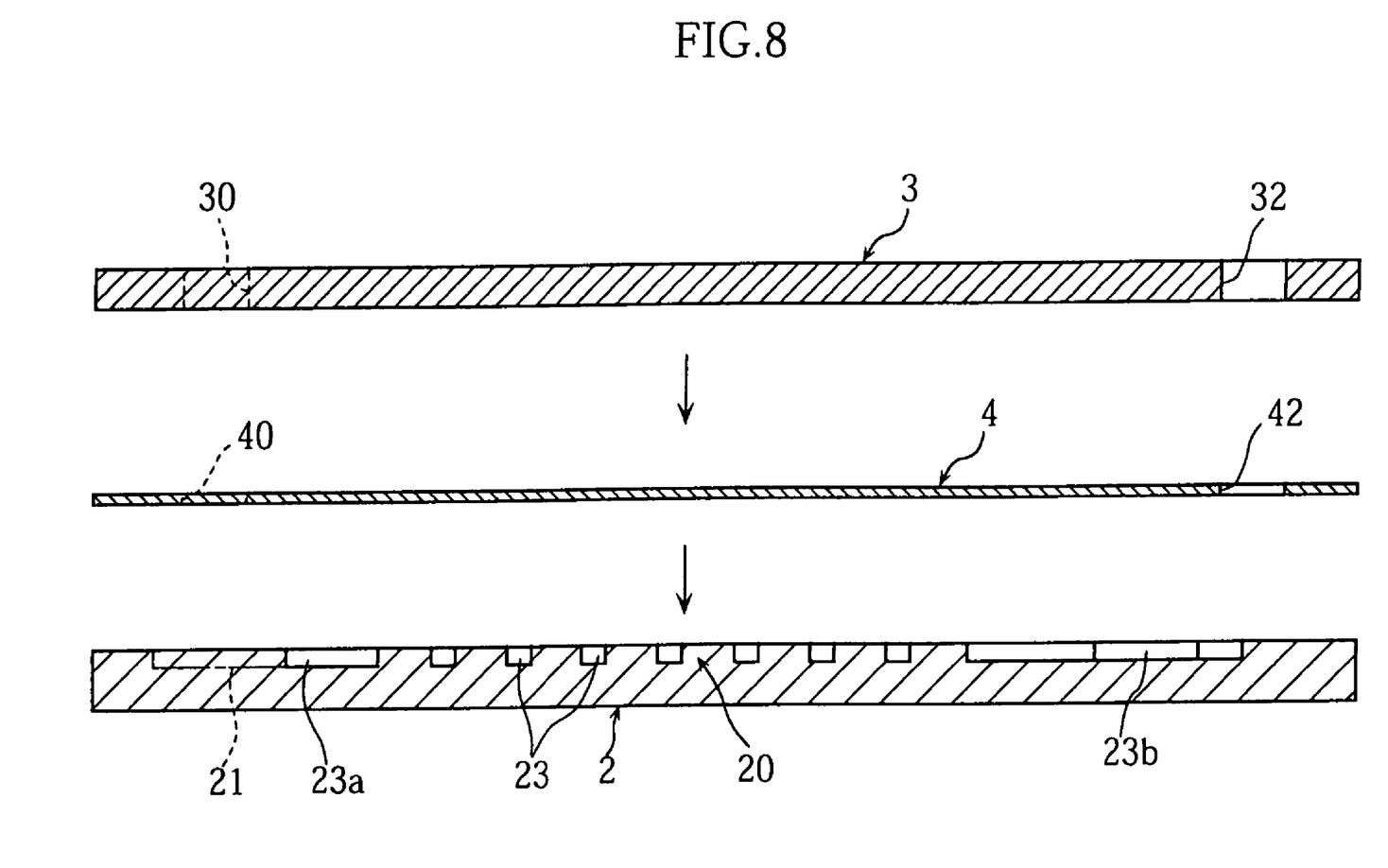
FIG. 8 is a sectional view showing a bonding step in the production method of the present invention.

For example, the bonding step is performed by interposing an adhesive sheet 4 between the substrate 2 and the cover 3, and then applying a pressing force to the adhesive sheet 4, as shown in FIG. 8. As the adhesive sheet 4, use may be made of whose opposite surfaces are adherent and which is formed with openings 40 and 42 at locations corresponding to the sample introduction port 30, the reagent introduction port 31 and the air vent 32 of the substrate 2.

In the hydrophilization step of this embodiment, the primary modifying step is performed by using a modifying gas (gas), whereas the secondary modifying step is performed by using gas or liquid such as water vapor or water. Since these substances do not have such linearity as that of ultraviolet rays, the substances such as a modifying gas and water vapor can be reliably brought into contact with the inner surface of the groove 20. Therefore, the entirety of the inner surface of the groove 20 can be hydrophilically treated reliably. Such an advantage can be obtained also in producing a microdevice 1 including a small flow path (a groove 20 having a small sectional area). Moreover, since the apparatus for supplying a modifying gas, water or water vapor can have a simple structure and can be manufactured at a low cost, the method is advantageous also in terms of the manufacturing cost.

The present invention is not limited to the foregoing embodiments but may modified in various ways. For example, although the hydrophilization with respect to the substrate is performed before the cover is bonded to the substrate in the foregoing embodiments, the hydrophilization may be performed after the cover is bonded to the substrate. In such a case, not only the inner surface of the groove but also the surface of the cover which faces the flow path can be hydrophilically treated.

The present invention is also applicable to such microdevices as one that mixes three or more liquids, one that is formed with a plurality of fluid paths for providing a plurality of reaction systems, and one which contains a reagent in the fluid path so that only a sample liquid is introduced to the fluid path. The present invention is also applicable to microdevices for analyzing a sample by an electrochemical method as well as those for analyzing a sample by an optical method.

The present invention is also applicable to the case where a plurality of analytical tools are to be produced at the same time. For example, a plate member including a plurality of portions which are later to become substrates may be formed by resin-molding, and then the plate member may be hydrophilically treated. In this case, another plate member including a plurality of portions which are to become covers is bonded to the plate member, and then the bonded product is cut, whereby a plurality of analytical tools are provided at the same time.

In the foregoing embodiments, an adhesive sheet and a cover in which through-holes are formed in advance are bonded to the substrate. However, through-holes may be formed in the adhesive sheet and the cover after the adhesive sheet and the cover are bonded to the substrate.

The bonding of the cover to the substrate may not necessarily be performed by using the adhesive sheet. For example, the bonding may be performed by using an adhesive or by heat seal or ultrasonic fusing.

According to the present invention, hydrophilization can be properly performed not only with respect to a groove having a rectangular cross section but also to a groove having another cross sectional configuration such as a semi-circular cross section or a triangular cross section.

The invention claimed is:

1. A method of producing an analytical tool comprising a substrate made of polymethyl methacrylate having a keto group and formed with a groove for moving a sample liquid, and a cover bonded to the substrate to cover the groove, the method comprising:
hydrophilically treating an inner surface of the groove of the substrate; and
bonding the cover to the hydrophilized substrate;
wherein the hydrophilization for the substrate includes a primary modifying step for bringing a modifying gas into contact with the inner surface of the groove to cause a primary substitution group from the modifying gas to bond to the keto group of the polymethyl methacrylate, and a secondary modifying step for substituting the primary substitution group bonded to the keto group with a hydroxyl group.

2. The analytical tool producing method according to claim 1, wherein the modifying gas contains fluorine gas and oxygen gas.

3. The analytical tool producing method according to claim 2, wherein mixing ratio of the fluorine gas and the oxygen gas is 1:1~1000 on a volume basis.

4. The analytical tool producing method according to claim 3, wherein mixing ratio of the fluorine gas and the oxygen gas is 1:10~20 on a volume basis.

5. The analytical tool producing method according to claim 1, wherein the primary modifying step is performed for 1~60 minutes under conditions where partial pressure of the modifying gas is maintained at 10~2000 hPa and temperature is maintained at 0~100° C.

6. The analytical tool producing method according to claim 5, wherein the partial pressure of the modifying gas is maintained at 100~1100 hPa and the temperature is maintained at 0~40° C.

7. The analytical tool producing method according to claim 1, wherein the secondary modifying step comprises bringing water or water vapor into contact with the inner surface of the groove.

8. The analytical tool producing method according to claim 7, wherein the bringing of water or water vapor into contact with the inner surface of the groove comprises spraying water or water vapor to an inner surface of the substrate.

9. The analytical tool producing method according to claim 7, wherein the bringing of water or water vapor into contact with the inner surface of the groove comprises immersing the substrate in a water bath.

10. The analytical tool producing method according to claim 7, wherein the bringing of water or water vapor into contact with the inner surface of the groove comprises leaving the substrate in air.

11. The analytical tool producing method according to claim 10, wherein the air is positively caused to contain moisture.

12. The analytical tool producing method according to claim 1, wherein the hydrophilization treatment for the substrate is so performed that a contact angle of pure water at the inner surface of the groove becomes 0~80 degrees.

13. The analytical tool producing method according to claim 12, wherein the contact angle is 0~60 degrees.

14. The analytical tool producing method according to claim 1, wherein the analytical tool is designed to move the sample liquid by capillary action.

15. The analytical tool producing method according to claim 14, wherein the groove has a principal, rectangular cross section which has a width W of 10~500 μm and a depth D of 5~500 μm and which satisfies $D/W \geqq 0.5$.

* * * * *